(12) United States Patent
Fukuda

(10) Patent No.: US 7,371,472 B2
(45) Date of Patent: May 13, 2008

(54) PERMANENT MAGNET RING

(75) Inventor: Shigeo Fukuda, Sagamihara (JP)

(73) Assignee: Sagami Chemical Metal Co., Ltd., Kanagawa (JP)

( * ) Notice: Subject to any disclaimer, the term of this patent is extended or adjusted under 35 U.S.C. 154(b) by 0 days.

(21) Appl. No.: 10/735,613

(22) Filed: Dec. 16, 2003

(65) Prior Publication Data

US 2004/0126621 A1 Jul. 1, 2004

(30) Foreign Application Priority Data

Dec. 24, 2002 (JP) ............................ 2002-008153
Oct. 30, 2003 (JP) ............................ 2003-370241

(51) Int. Cl.
A47G 35/00 (2006.01)
B32B 15/04 (2006.01)
A44C 5/00 (2006.01)
A44C 25/00 (2006.01)

(52) U.S. Cl. .................. 428/693.1; 63/3.1; 63/3.2; 63/41; 63/900; 428/33; 428/357; 428/403; 428/542.2

(58) Field of Classification Search ............. 428/692.1; 63/3, 3.1, 900; 600/15
See application file for complete search history.

(56) References Cited

U.S. PATENT DOCUMENTS

| 3,885,383 | A | * | 5/1975 | Tanaka | ......................... | 59/79.1 |
|---|---|---|---|---|---|---|
| 4,067,783 | A | * | 1/1978 | Okinaka et al. | ............... | 205/81 |
| 4,095,587 | A | * | 6/1978 | Ishikawa | ....................... | 600/15 |
| 4,517,217 | A | * | 5/1985 | Hoffman | ....................... | 428/632 |
| 4,981,532 | A | * | 1/1991 | Takeshita et al. | ............ | 148/302 |
| 5,195,335 | A | * | 3/1993 | Hart | .............................. | 63/3.2 |
| 5,347,253 | A | * | 9/1994 | Ogikubo | ..................... | 335/302 |
| 5,535,603 | A | * | 7/1996 | Hayakawa | ........................ | 63/3 |
| 6,427,486 | B1 | * | 8/2002 | Yellen | .............................. | 63/3 |
| 6,634,067 | B2 | * | 10/2003 | Jacobson | ...................... | 24/618 |
| 2004/0111005 | A1 | * | 6/2004 | Lu | .............................. | 600/15 |
| 2005/0148809 | A1 | * | 7/2005 | Delaney | ...................... | 600/15 |

FOREIGN PATENT DOCUMENTS

| GB | 2285222 A | * | 7/1995 |
| GB | 2287884 A | * | 10/1995 |
| JP | 3021225 | | 11/1995 |
| JP | 3033643 | | 11/1996 |
| JP | 11-103915 | * | 4/1999 |

OTHER PUBLICATIONS

Web article titled "Rare-earth magnet" (Rare-earth magnet—Wikipedia, the free encylocpedia, modified Jan. 17, 2006).*
English Translation of JP 11-103915 A (PTO 2006-4245).*
Magnetism FAQs (http://www.matchrockets.com/ether/magfaqs.html), updated Jan. 24, 2002, pp. 1-9.*
Electromagnetics Explained (Ron Schmitt, 2002 by Elsevier Science, USA), pp. 51-74.*
English Translation of JP 11-103915 A (PTO 07-2945).*

* cited by examiner

Primary Examiner—Kevin M. Bernatz
(74) Attorney, Agent, or Firm—Bacon & Thomas PLLC

(57) ABSTRACT

In a permanent magnet ring (1) formed by arranging a plurality of unit permanent magnets (21a, 21b, 21c . . . ), each of a plurality of the unit permanent magnets (21a, 21b, 21c . . . ) is formed in a circular cylindrical shape having a circular cross section, and a predetermined number of the unit permanent magnets are magnetically attracted each other so as to form a ring shape having a predetermined size, so that it is possible for the user to easily structure the permanent magnet ring (1) having a desired size, and it is possible to attach as many the unit permanent magnets as possible so as to be able to apply proper magnetic force lines to each part of the body.

3 Claims, 15 Drawing Sheets

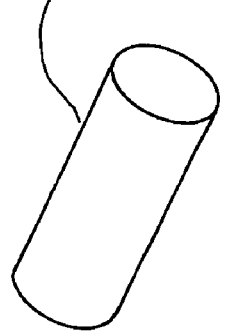
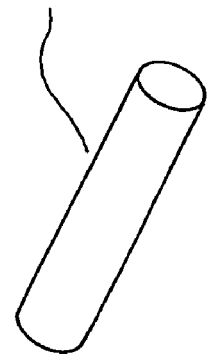
FIG. 7 (a)  FIG. 7 (b)
FIG. 8
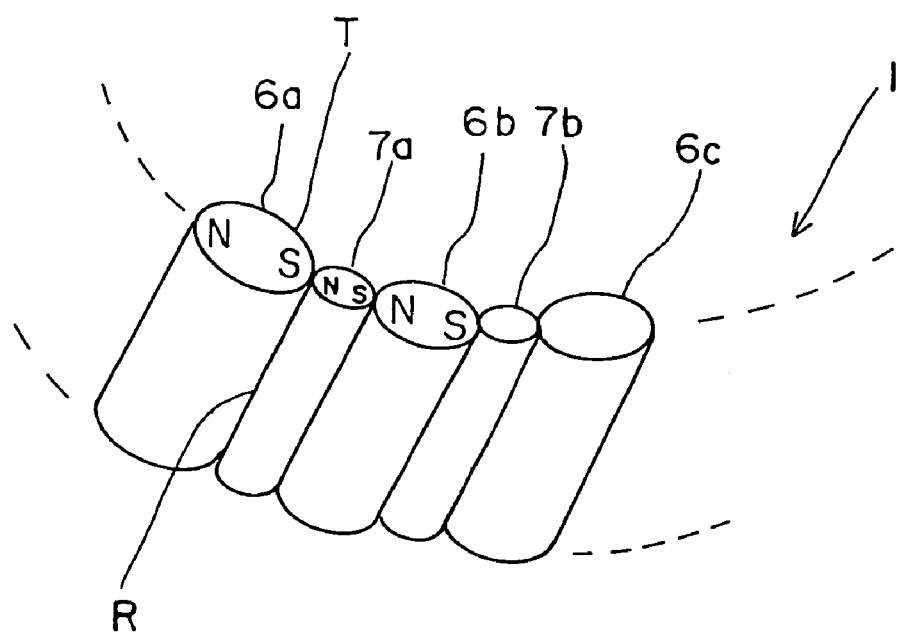

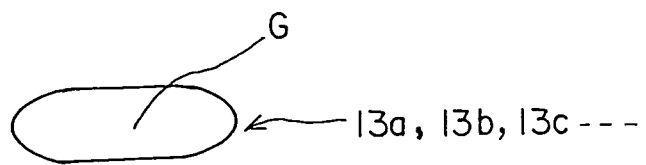
FIG. 13 (b)
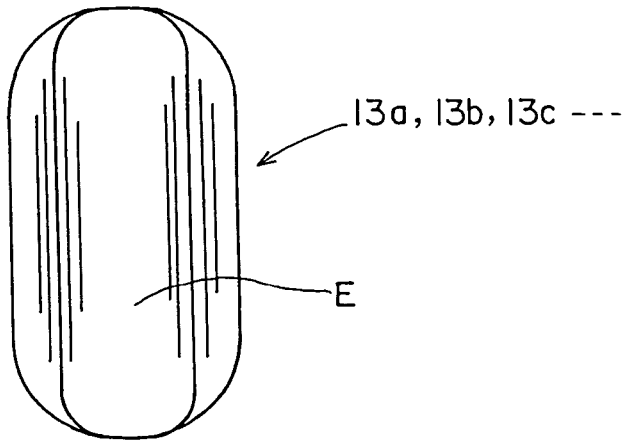
FIG. 13 (a)
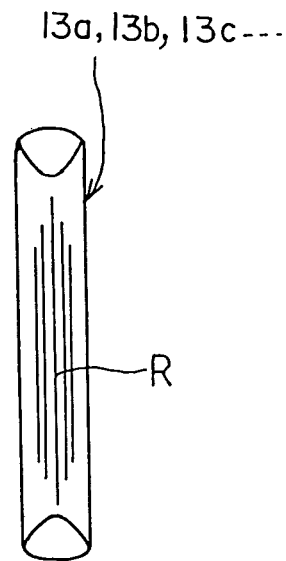
FIG. 13 (c)
FIG. 14
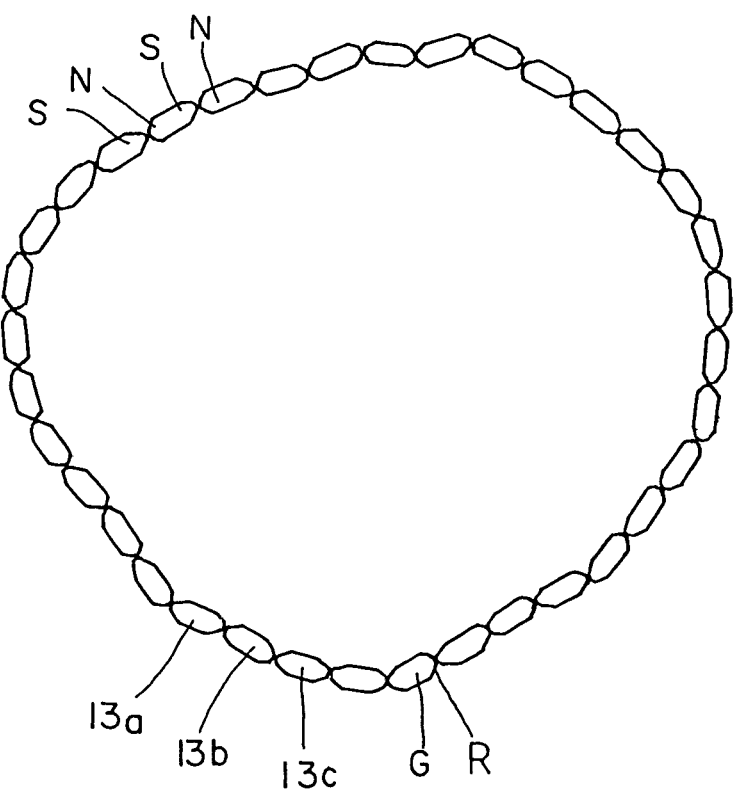

PERMANENT MAGNET RING

BACKGROUND OF THE INVENTION

1. Field of the Invention

The present invention relates to a permanent magnet ring, and more particularly to an improvement of a permanent magnet ring which is worn on a wrist, an ankle, a portion around a neck, a portion around an arm, a portion around a leg and the like, and facilitates the flow of blood on the basis of an operation of magnetism output from the permanent magnet ring.

2. Description of Conventional Art

As is well known, a lot of permanent magnet rings have been put to practical use as an ornamental on a body such as a necklace or a bracelet which is worn on a wrist, an ankle, a portion around a neck or the like with expection to facilitate the flow of blood on the basis of the magnetic operation of the magnetism output from the permanent magnet ring, and have been proposed as inventions.

One of the conventional arts is Japanese Utility Model No. 3033643. In this invention, there is described a health appliance utilizing magnetism constituted by an elastic ring which is curved and in which both ends are opposed, and four magnets which are fixed to the ring. In the health appliance, two of the magnets mentioned above are fixed so as to contact with pressure to an arteria carotis at a time of wearing the ring mentioned above around a neck, the residual two magnets are fixed so as to contact with pressure to positions apart from a center portion of a nape toward both sides by a predetermined distance, both end portions of the ring are connected by a connecting means, and a size of the ring mentioned above can be adjusted by the connecting means.

Another of the conventional arts is Japanese Utility Model No. 3021225. In this invention, there is described a health accessory such as a necklace, a bracelet or the like worn on a neck, a wrist or the like of a human body in which an accessory base bodies are connected in a chain shape by a lot of connecting members. In the health accessory, a coating main agent is formed by mixing a liquefied resin such as a silicone or the like, a micro powder mineral obtained by crushing various kinds of minerals such as a serpentine, an amphibolite, a zeolite, a fluorite, a fergusonite and the like, and a micro powder plant obtained by drying a moss plant such as a hair moss, a hepatica or the like and then making them into powder, a lot of chip-shaped base agents are formed by coating a permanent magnet with the coating main agent and thereafter applying a heat treatment, and the base agent is buried in a recess portion formed on the surface of the accessory base body to be contacted on a human body.

In the case of the conventional embodiment 1 and the conventional embodiment 2 mentioned above, the structure is made such that the permanent magnet is fixed to the connecting member. In the case of Japanese Utility Model No. 3033643, a container is fixed to the ring and the permanent magnet is arranged in the container. In the case of another Japanese Utility Model No. 3021225, the permanent magnet is buried in the base body and such the base bodies are connected in the ring shape.

In the case of the conventional arts mentioned above, the container or the base body is provided for the purpose of fixing the permanent magnet on the ring or in the ring-shaped arrangement position, and the permanent magnet is buried therein, thereby structuring the health appliance or the health accessory utilizing the magnetism. Accordingly, there are problems that a lot of manufacturing steps are required and a manufacturing cost is increased. Further, since the container or the base body is required and has a certain size, the number of the permanent magnets which can be mounted around one ring tends to be reduced. Therefore, in the case of the conventional health appliance and the conventional health accessory utilizing the magnetism, there is a problem that an effect of magnetic force lines applied by the permanent magnet on each of portions of the human body tends to be reduced.

SUMMARY OF THE INVENTION

Accordingly, an object of the present invention is to provide a permanent magnet ring which can be easily structured in an optional size by users themselves, and to provide a permanent magnet ring in which as many unit permanent magnets as possible can be mounted around one ring, and density of magnetic force lines applied to each of portion of the human body of a user is rich.

Especially, an object of the present invention is to provide a permanent magnet ring in which the user can freely set the number of the unit permanent magnets constituting the permanent magnet ring, whereby it is possible to optionally set the size of the permanent magnet ring so as to improve comfortableness for wearing on each of the portions of the human body of the user at a time of using as a necklace or a bracelet.

Further, another object of the present invention is to provide a permanent magnet ring in which strong magnetic attraction is obtained between a plurality of unit permanent magnets constituting the permanent magnet ring without using a mechanical connecting means such as a wire or the like, and the ring shape can be firmly kept without each of the unit permanent magnets coming off in the case of wearing the permanent magnet ring on an arm, a neck, an ankle or the like.

Further, another object of the present invention is to provide a permanent magnet ring which can set magnetic force lines applied to an arm, a neck, an ankle or the like on which the permanent magnet ring is worn to a suitable level for facilitating the flow of blood, even though the magnetic attraction power between a plurality of unit permanent magnets constituting the permanent magnet ring is strong as mentioned above, thereby preventing an unexpected side effect from being generated.

Further, another object of the present invention is to provide a permanent magnet ring in which the unit permanent magnets do not easily break away from each other in a breaking away direction due to a strong magnetic attraction between the unit permanent magnets constituting the permanent magnet ring, and a position of attraction in a non-breaking away direction can be easily changed, so that a ring shape can be easily formed at a time of a plurality of the unit permanent magnets attracting each other.

In order to achieve the object mentioned above, the present invention has the following technical means. The present invention is described by attaching reference numerals used in the accompanying drawings shown in the embodiment below. In accordance with the present invention, there is provided a permanent magnet ring 1 formed by arranging a plurality of unit permanent magnets $5a$, $5b$, $5c$, $5d$ . . . , wherein each of a plurality of the unit permanent magnets $5a$, $5b$, $5c$, $5d$ . . . is formed to have a circular cross section and in a cylindrical shape as a whole, and a predetermined number of the unit permanent magnets $5a$, $5b$, $5c$, $5d$ . . . formed in the cylindrical shape are magnetically attracted each other on respective side surfaces R so as to form a ring shape having a predetermined size.

Further, there is provided a permanent magnet ring 1 formed by arranging a plurality of unit permanent magnets 12a, 12b, 12c . . . , wherein each of a plurality of the unit permanent magnets 12a, 12b, 12c . . . is formed in a spherical shape, and a predetermined number of the unit permanent magnets 12a, 12b, 12c . . . formed in the spherical shape are magnetically attracted each other on respective peripheral surfaces so as to form a ring shape having a predetermined size.

Further, there is provided a permanent magnet ring 1 formed by arranging a plurality of unit permanent magnets 13a, 13b, 13c . . . , wherein each of a plurality of the unit permanent magnets 13a, 13b, 13c . . . is formed in a flat shape, and a predetermined number of the unit permanent magnets 13a, 13b, 13c . . . formed in the flat shape are magnetically attracted each other on respective side surfaces R so as to form a ring shape having a predetermined size.

In addition, there is provided a permanent magnet ring 1 formed by arranging a plurality of unit permanent magnets 14a, 14b, 14c . . . , wherein each of a plurality of the unit permanent magnets 14a, 14b, 14c . . . is formed in a disc shape, and a predetermined number of the unit permanent magnets 14a, 14b, 14c . . . formed in the disc shape are magnetically attracted each other on respective surfaces R so as to form a ring shape having a predetermined size, and there is provided a permanent magnet ring, wherein a plated layer is formed on a surface of the unit permanent magnet, and a transparent siliceous coating layer is formed over the plated layer.

Further, in accordance with the present invention, there is provided a permanent magnet ring formed by arranging a plurality of unit permanent magnets 21a, 21b, 21c . . . , wherein each of the unit permanent magnets 21a, 21b, 21c . . . is formed in a cylindrical shape, a spherical shape, a flat shape, a disc shape or the like, and a predetermined number of the unit permanent magnets 21a, 21b, 21c . . . are magnetically attracted each other on respective side surfaces R so as to be formed in a ring shape, wherein each of a plurality of the unit permanent magnets 21a, 21b, 21c . . . is a rare earth magnet such as a neodymium iron boron magnet, a samarium cobalt magnet and the like, and is a uniaxial anisotropic magnet in which an N pole or an S pole is formed on one part of the side surface R orthogonal to an easily magnetizing direction X-X, which is formed at a time of molding a raw material including a rare earth element in a magnetic field, by magnetizing along the easily magnetizing direction X-X after sintering, and the S pole or the N pole is formed on another part of the side surface R opposite to the above one part of the side surface, the side surface R, on which the magnetic poles of the unit permanent magnet are formed, is formed to be a curved surface, and a predetermined number of the unit permanent magnets 21a, 21b, 21c . . . , which are the uniaxial anisotropic magnets, are magnetically attracted each other in a line contact aspect or a point contact aspect on the curved side surfaces R on which the magnetic poles are formed, so as to be formed in a ring shape having a predetermined size.

Further, there is provided a permanent magnet ring, wherein the unit permanent magnets 21a, 21b, 21c . . . are formed in a circular cross sectional shape, and formed in a cylindrical shape as a whole, and a predetermined number of the unit permanent magnets 21a, 21b, 21c . . . are magnetically attracted each other in a line contact aspect on the curved side surfaces R on which the magnetic poles are formed, so as to be formed in a ring shape.

Further, there is provided a permanent magnet ring, wherein the unit permanent magnets 21a, 21b, 21c . . . are formed in a spherical shape, and a predetermined number of the unit permanent magnets 21a, 21b, 21c . . . are magnetically attracted each other in a point contact aspect on the curved side surfaces R on which the magnetic poles are formed, so as to be formed in a ring shape.

Further, there is provided a permanent magnet ring, wherein the unit permanent magnets 21a, 21b, 21c . . . are formed in a flat shape, and a predetermined number of unit permanent magnets 21a, 21b, 21c . . . are magnetically attracted each other in a line contact aspect on the curved side surfaces R on which the magnetic poles are formed, so as to be formed in a ring shape.

Further, there is provided a permanent magnet ring, wherein a plated layer is formed on a surface of the unit permanent magnet, and a transparent siliceous coating layer is formed over the plated layer.

Further, there is provided a method of manufacturing unit permanent magnets 21a, 21b, 21c . . . in a permanent magnet ring structured such that each of the unit permanent magnets 21a, 21b, 21c . . . constituting the permanent magnet ring is formed in a cylindrical shape, a spherical shape, a flat shape, a disc shape or the like, and a predetermined number of the unit permanent magnets 21a, 21b, 21c . . . are magnetically attracted each other on respective side surfaces R, comprising the steps of:

preparing an ingot on the basis of a raw material including a rare earth element;

crushing the ingot;

thereafter arranging crystals in a determined easily magnetizing direction X-X at a time of molding in a magnetic field;

manufacturing a block-shaped formed body in accordance with the molding in the magnetic field;

thereafter manufacturing a block-shaped sintered body by sintering;

next obtaining a plurality of unit permanent magnet raw materials by cutting;

working each of the unit permanent magnet raw materials in the cylindrical shape, the spherical shape, the flat shape, the disc shape or the like;

thereafter forming a plated layer and a siliceous coating layer on a surface thereof;

next forming an N pole or an S pole on one part of a side surface R orthogonal to the easily magnetizing direction X-X of each of the unit permanent magnets 21a, 21b, 21c . . . by magnetizing the above products along the easily magnetizing direction X-X, and the S pole or the N pole on another part of the side surface R opposite to the above one part of the side surface; and forming the side surface R on which the magnetic poles of the unit permanent magnet are formed, as a curved surface.

As in detail mentioned above, in accordance with the present inventions on the basis of the first, second, third and fourth aspect, it is possible to provide the permanent magnet ring in which the permanent magnet ring having an optional size can be easily structured by the user, and it is possible to provide the permanent magnet ring in which as many unit permanent magnets as possible can be attached around one ring, and the density of magnetic force lines applied to each of the body of the user is rich.

Especially, since the user can freely set the number of the unit permanent magnets constituting the permanent magnet ring, it is possible to optionally set the size of the permanent magnet ring, and it is possible to provide the permanent magnet ring having good comfortableness for wearing on each of the portions of the human body of the user at a time of being used as a necklace or a bracelet.

Further, in accordance with the present invention on the basis of the fifth aspect, in addition to the advantages mentioned above, it is possible to maintain an ornamental state such as gold plating for a long time.

Further, in accordance with the present inventions on the basis of the sixth, seventh, eighth and ninth aspects, the strong magnetic attraction is achieved between a plurality of unit permanent magnets constituting the permanent magnet ring without using a mechanical connecting means such as the wire or the like, and it is possible to provide the permanent magnet ring in which the ring shape can be firmly kept without the unit permanent magnets being broken away one by one during the time of wearing on the arm, the neck, the ankle or the like.

Further, it is possible to provide the permanent magnet ring which sets the magnetic force lines applied to an arm, a neck, an ankle or the like on which the permanent magnet ring is worn to a suitable level for facilitating the flow of blood, even though the magnetic attracting force between a plurality of unit permanent magnets constituting the permanent magnet ring as mentioned above, and has no fear that any unexpected side effect is generated.

Further, it is possible to provide the permanent magnet ring in which the unit permanent magnets constituting the permanent magnet ring do not break away easily in the breaking-away direction with each other due to the strong magnetic attraction between the unit permanent magnets, however, are easily changed in the attracting position with each other in the non-breaking-away direction so as to be formed easily in the ring shape at a time of a plurality of unit permanent magnets being attracted.

Further, in accordance with the present invention on the basis of the tenth aspect, in addition to the advantages mentioned above, it is possible to maintain the ornamental state such as gold plating for a long time.

In addition, in accordance with the present invention on the basis of the eleventh aspect, it is possible to provide the method of manufacturing the permanent magnet ring using a plurality of uniaxial anisotropic unit permanent magnets, and it is possible to easily manufacture the permanent magnet ring achieving the advantages mentioned above.

BRIEF DESCRIPTION OF THE DRAWINGS

FIGS. 7A and 7B are perspective views explaining a state in which cylindrical unit permanent magnets having different sizes from each other are formed;

FIG. 8 is a view showing an example in which a permanent magnet ring is structured by magnetically attracting the unit permanent magnets having the different sizes in FIG. 7;

FIGS. 12A and 12B show a cross section of the spherical unit permanent magnet, in which FIG. 12A is a cross sectional view of the spherical unit permanent magnet shown along a line 11-11 in FIG. 11, and FIG. 12B is a cross sectional view of the spherical unit permanent magnet shown along a line 12-12 in FIG. 11;

FIGS. 13A, 13B and 13C show a flat unit permanent magnet, in which FIG. 13A is a plan view, FIG. 13B is a top view and FIG. 13C is a side view;

FIG. 14 is a plan view of a permanent magnet ring constituting a plurality of flat unit permanent magnets in accordance with the embodiment shown in FIG. 13;

FIGS. 15A and 15B show a state in which disc-shaped unit permanent magnets are magnetically attracted with each other, in which FIG. 15A is a plan view and FIG. 15B is a top view;

FIGS. 16A and 16B show a state in which approximately rectangular unit permanent magnets are magnetically attracted with each other, in which FIG. 16A is a plan view and FIG. 16B is a top view;

DESCRIPTION OF THE PREFERRED EMBODIMENTS

Next, a description will be given below of a preferable embodiment in accordance with the present invention with reference to the accompanying drawings.

Figure 1:
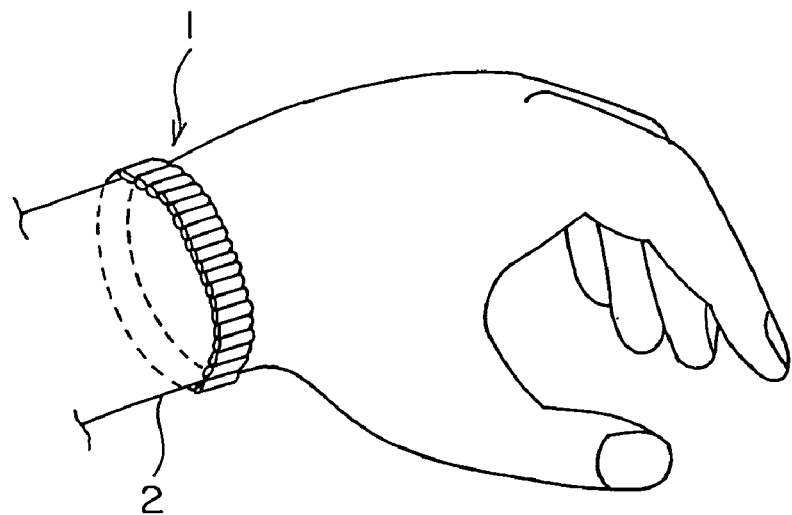
FIG. 1 is a view showing a state in which a permanent magnet ring in accordance with an embodiment of the present invention is worn on a wrist.
Figure 2:
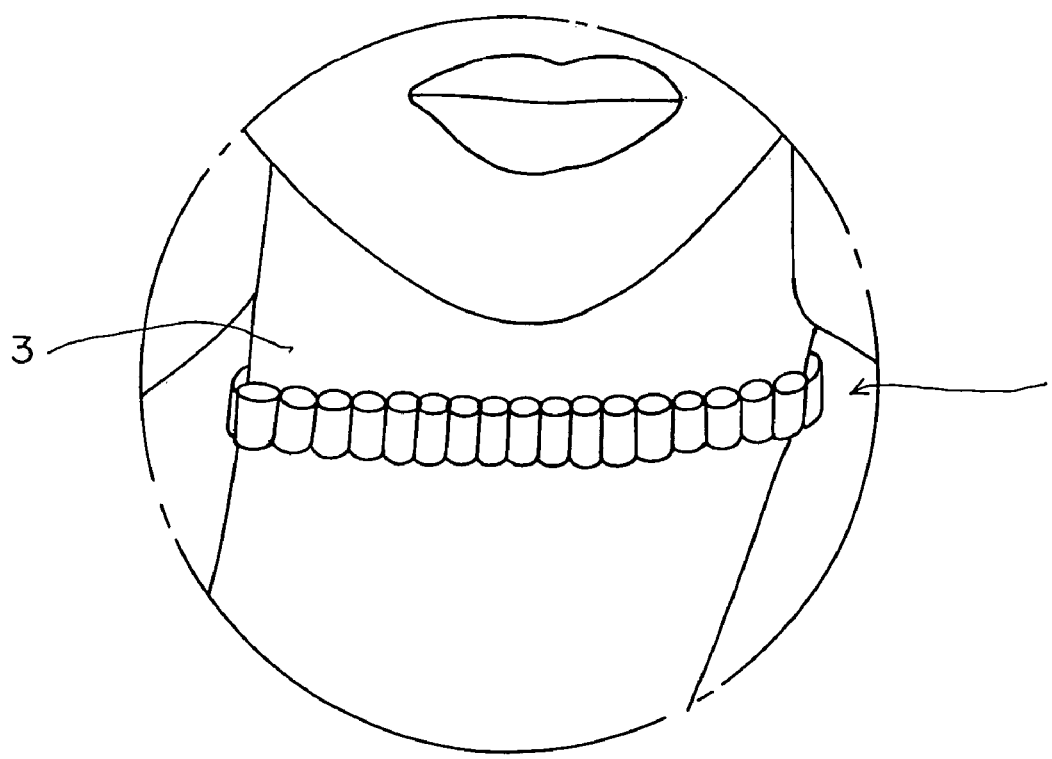
FIG. 2 is a view showing a state in which a permanent magnet ring in accordance with an embodiment of the present invention is worn on a neck.
Figure 3:
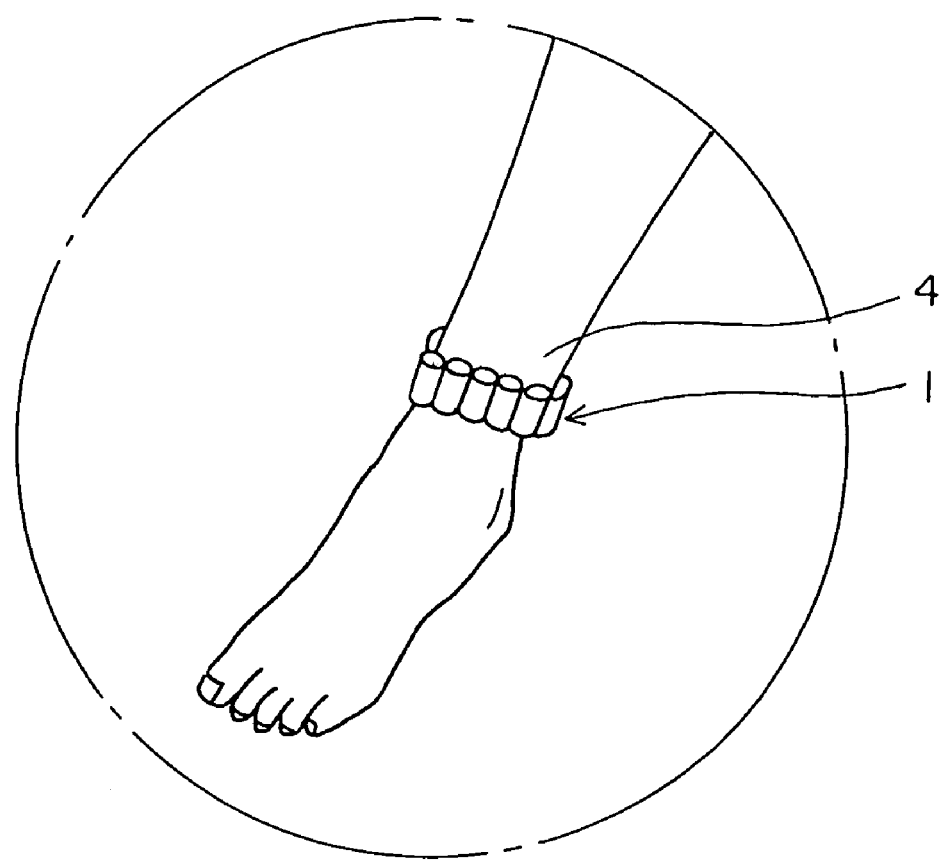
FIG. 3 is a view showing a state in which a permanent magnet ring in accordance with an embodiment of the present invention is worn on an ankle.

A permanent magnet ring 1 in accordance with the present invention is used in a state of being attached to a wrist 2 of a user as illustrated in FIG. 1, or is used in a state of being attached around a neck 3 as illustrated in FIG. 2, or is used in a state of being attached to an ankle 4 as illustrated in FIG. 3. In addition, the permanent magnet 1 can be used as a finger ring, a wrist band, a foot ring or the like although an illustration is omitted.

Figure 4:
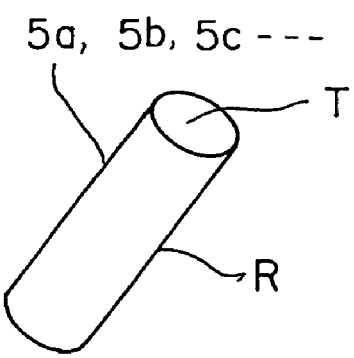
FIG. 4 is a perspective view showing an example of a cylindrical unit permanent magnet constituting the permanent magnet ring in accordance with the embodiment.
Figure 5:
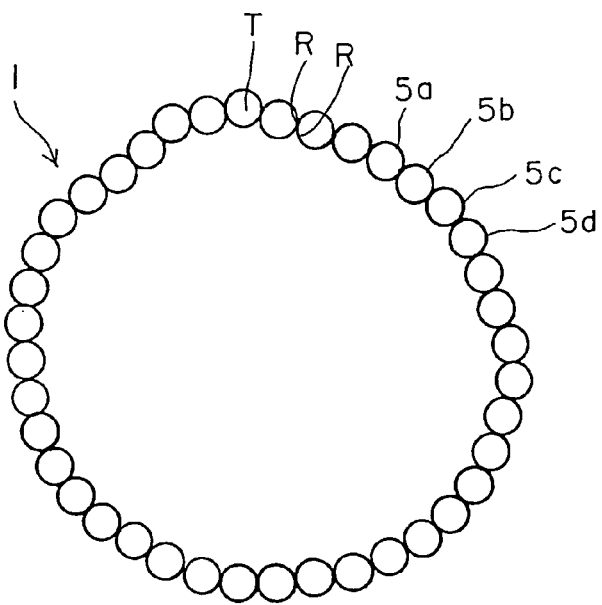
FIG. 5 is a view showing a plane shape of the permanent magnet ring in accordance with the embodiment in FIG. 4.
Figure 6:
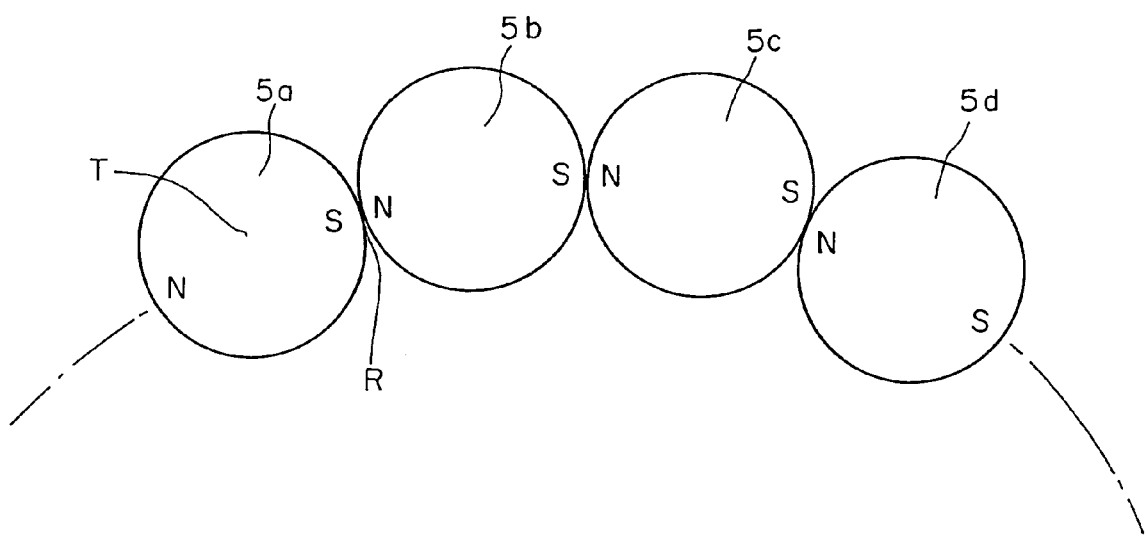
FIG. 6 is a view showing a state in which a plurality of unit permanent magnets in FIG. 4 are connected to each other in accordance with a magnetic attraction.

The permanent magnet ring 1 mentioned above is structured by connecting a lot of unit permanent magnets 5a, 5b, 5c, 5d . . . as shown in FIG. 4 to each other in accordance with a magnetic attraction as shown in FIG. 5. In an embodiment shown in FIGS. 4, 5 and 6, there is shown a structure in which a cross sectional shape of each of the unit permanent magnets 5a, 5b, 5c, 5d . . . mentioned above is formed to be circular, and an entire shape is formed in a cylindrical shape. Further, a desired size can be easily achieved by connecting a predetermined number of the cylindrically formed unit permanent magnets 5a, 5b, 5c, 5d . . . in accordance with a magnetic attraction. In this case, when giving a symbol T to both end surfaces of the cylinder in each of the cylindrical unit magnets 5a, 5b, 5c, 5d . . . , and a symbol R to a peripheral surface in the diametrical direction, each of the unit magnets 5a, 5b, 5c, 5d . . . is magnetically attracted with each other on the peripheral surface R thereof, as shown in FIGS. 5 and 6. Further, various rings having various sizes can be optionally structured in correspondence to a portion to be applied, such as a portion around an arm, an ankle 4, a portion around a foot, a portion around neck 3 and the like in addition to the wrist 2 as shown in FIGS. 1, 2 and 3, by structuring in a desired size.

FIG. 5 shows a state in which each of the permanent magnets 5a, 5b, 5c, 5d . . . is connected in accordance with the magnetic attraction. The permanent magnet ring 1 in accordance with the present embodiment is structured such that the permanent magnets 5a, 5b, 5c, 5d . . . are connected to each other in different magnetic poles such as N pole→S pole→N pole→S pole→N pole→S pole . . . on the peripheral surfaces (the side surfaces) R thereof. Accordingly, each of the permanent magnets 5a, 5b, 5c, 5d . . . can be connected to each other on the basis of a strong magnetic attracting force, and it is possible to prevent the permanent magnets 5a, 5b, 5c, 5d . . . from being accidentally broken away during use.

Each of the unit permanent magnets 5a, 5b, 5c, 5d . . . is a magnet, for example, formed by a iron-boron rare earth. In recent years, the permanent magnet including the rare earth element as one of main components has been attracted attention in many fields since a strong magnetic force can be obtained. The unit permanent magnets 5a, 5b, 5c, 5d . . . are manufactured by molding and sintering, thereafter finishing to a predetermined size by a machine working or a grinding work, and applying a plating or the like. One example of the manufacturing method will be described in detail later with reference to FIG. 17.

In this case, in the case of applying the plating mentioned above, as shown in a cross sectional view in FIG. 9, a base layer 9 made of copper, nickel plating or the like is formed, for example, at a thickness of 20 to 25 micron on a surface of a rare earth 8 constituting the unit permanent magnets 5a, 5b, 5c, 5d . . . , and a gold or a platinum rhodium plating layer 10 is formed over a surface of the copper or nickel plating layer 9. In the case of forming the gold plating layer 10 mentioned above, a layer of about 1 to 1.5 micron is formed, for example, a gold-cobalt layer. In this case, for example, a platinum plating may be employed in place of the gold plating.

Further, in the example illustrated in FIGS. 4, 5 and 6, the unit permanent magnets 3a, 3b, 3c, 3d . . . have all the same size, and the strengths of the magnetic forces of the magnetic poles are defined the same, however, the strengths of the magnetic forces of the permanent magnet poles may be differentiated.

For example, unit permanent magnets 6a, 6b, 6c . . . shown in FIG. 7A are the same as the unit permanent magnets 5a, 5b, 5c . . . shown in FIG. 4, however, may be structured such that they have different diameters, that is, unit permanent magnets 7a, 7b . . . may be structured to have diameters narrower than the diameters of the permanent magnets 6a, 6b, 6c . . . (FIG. 7B). For example, the structure may be made such that the diameters of the permanent magnets 5a, 5b, 5c . . . , 6a, 6b, 6c . . . , 7a, 7b . . . are set to 3Φ, 4Φ, 5Φ, and lengths thereof are set to about 1 cm.

For example, the finger ring, the necklace or the like may be structured by magnetically attracting the narrow unit permanent magnets 7a, 7b . . . with each other in a ring shape as mentioned above while utilizing the property of narrowness. Further, an artistic bracelet may be structured by alternately magnetically attracting the permanent magnets in such a way as the permanent magnets 6a, 6b, 6c . . . → the permanent magnets 7a, 7b . . . → the permanent magnets 6a, 6b, 6c . . . → the permanent magnets 7a, 7b . . . → the permanent magnets 6a, 6b, 6c . . . so as to form a bracelet 1, as shown in FIG. 8.

Further, in the case that the bracelet or the like is structured by alternately magnetically attracting the unit permanent magnets plated with gold and the unit permanent magnets plated with platinum, it is possible to structure a bracelet which is rich in fashionableness.

In the case that the permanent magnet ring 1 in accordance with the present embodiment is worn as the necklace, the bracelet or the like on the portion to be worn such as the wrist, the portion around the arm, the ankle, the portion around the foot, the portion around the neck and the like of the human body, a strong line of magnetic force passes between the different poles N, S in the respective unit permanent magnets, so that the strong line of magnetic force is applied to the portion to be worn in the human body, and it is possible to facilitate the flow of blood in the portion and the peripheral portion.

Figure 9:
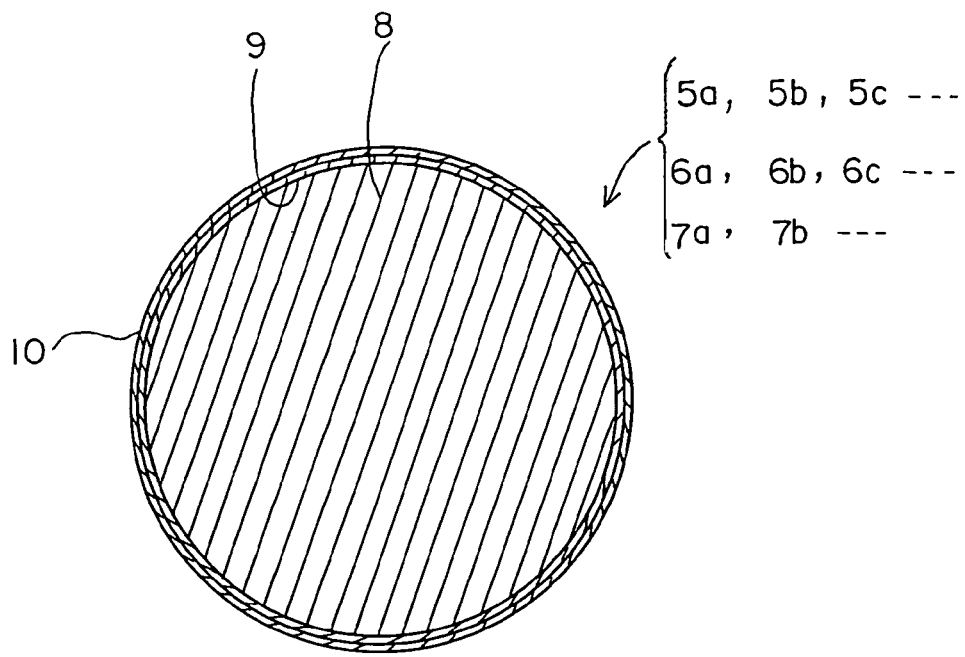
FIG. 9 is a cross sectional view showing an example in which a copper or nickel plating layer is formed on a rare earth surface of the cylindrical unit permanent magnet in FIG. 4, and a gold or platinum rhodium plating layer is formed thereon.
Figure 10:
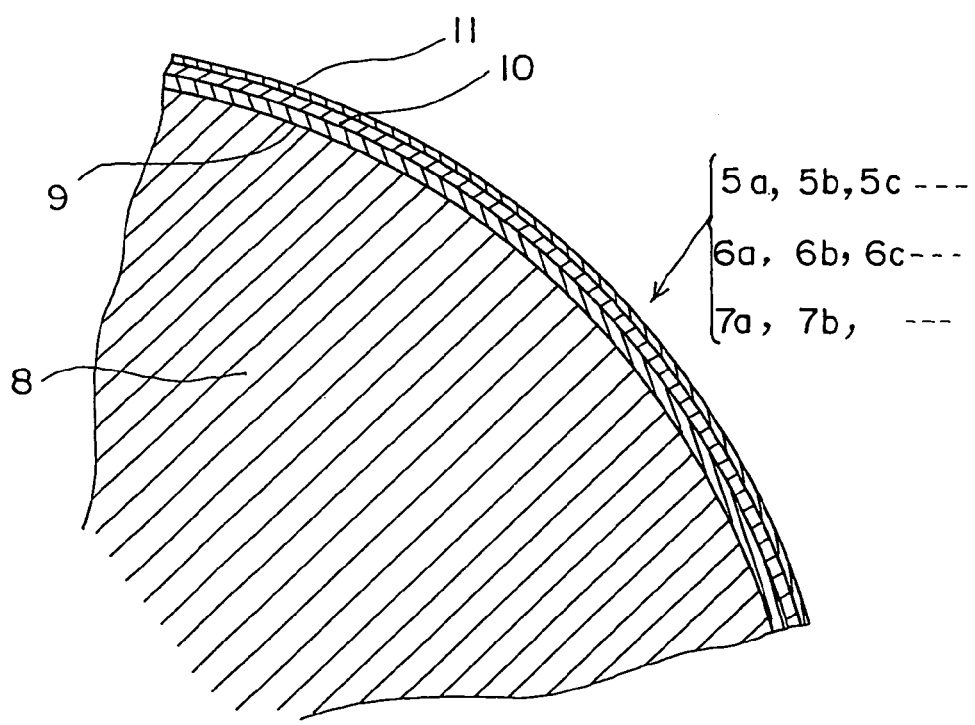
FIG. 10 is a partly cross sectional view showing a state in which a siliceous transparent coating layer is formed further on the plating layer of the unit permanent magnet in FIG. 9.

FIG. 9 shows the embodiment in which the plating layers 9 and 10 are formed on the unit permanent magnets 5a, 5b, 5c . . . , 6a, 6b, 6c . . . , 7a, 7b . . . , however, in the case that a transparent siliceous coating layer 11 is further formed on the surface of the plating layers as shown in FIG. 10, it is possible to achieve a corrosion prevention even when the wearer of the permanent magnet ring 1 sweats, so that it is possible to keep a brilliance of gold color or the like. A description of forming the transparent silica layer 11 will be in detail given later at a time of describing a method of manufacturing the unit permanent magnet or the permanent magnet ring with reference to FIG. 17.

While the description is given of the example of the cylindrical unit permanent magnet in the above embodiment, a description will be given of a unit permanent magnet and a permanent magnet ring in accordance with another embodiment with reference to FIGS. 11 to 16.

Figure 11:
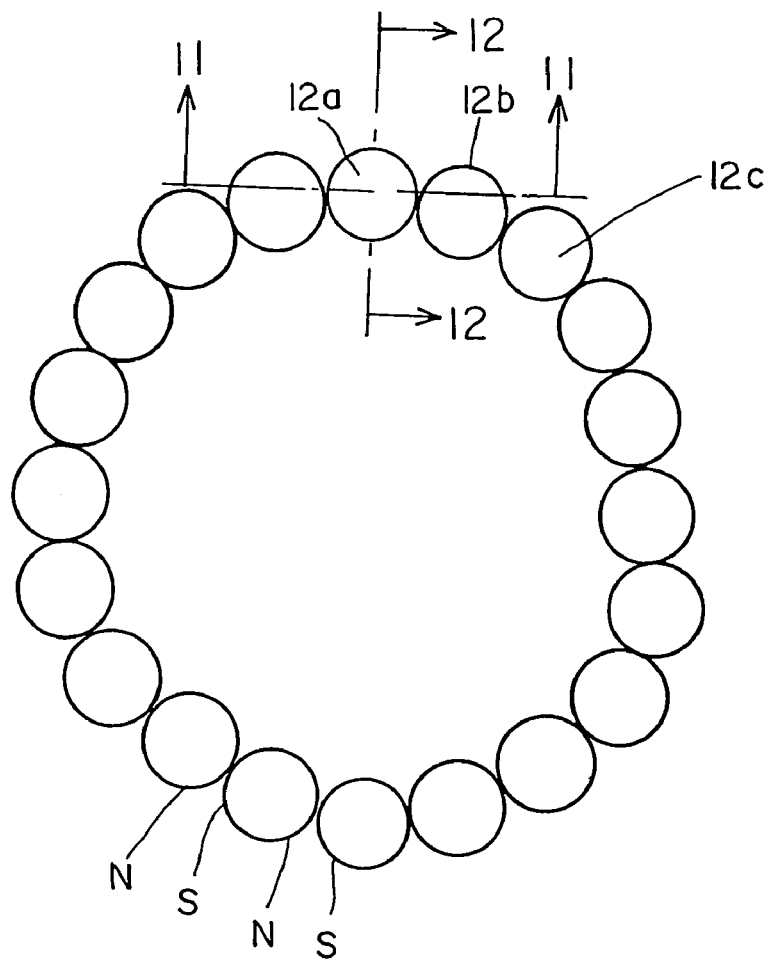
FIG. 11 is a plan view showing a permanent magnet ring constituted by a plurality of spherical unit permanent magnets.
Figure 12:
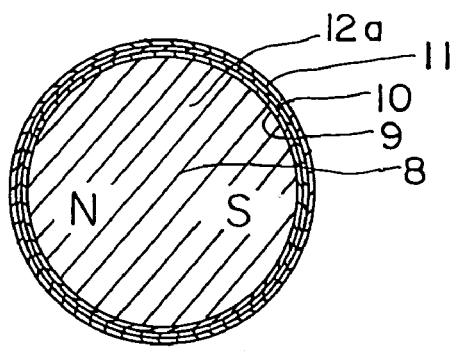
Figure 12:
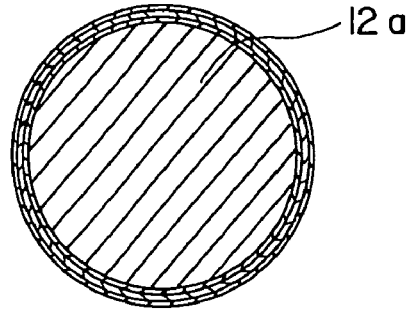
Figure 15:
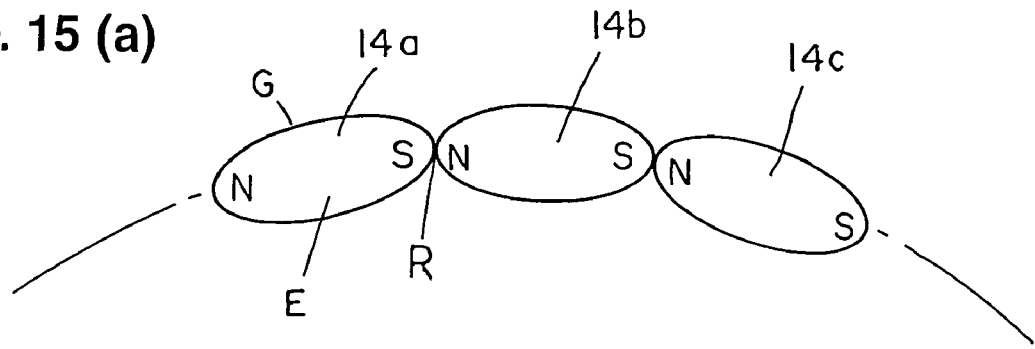
Figure 15:
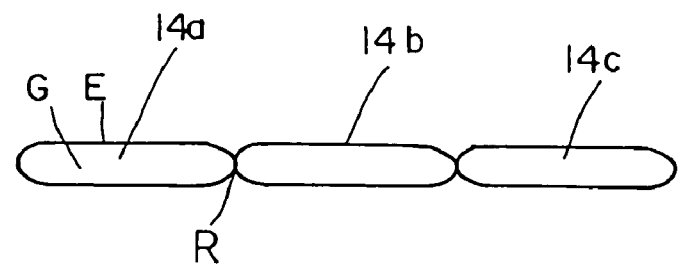
Figure 16:
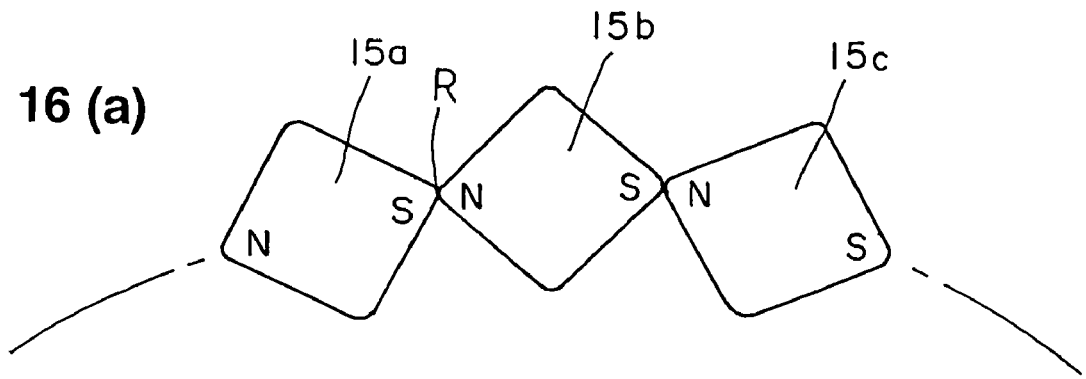
Figure 16:
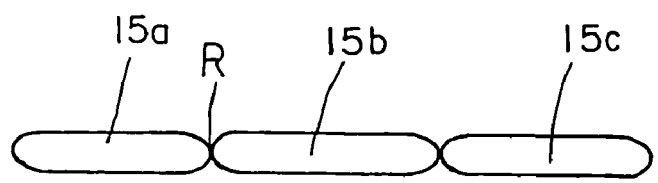

The example shown in FIGS. 11 and 12 corresponds to an example in which each of the unit permanent magnets 12a, 12b . . . is formed in a spherical shape. A cross sectional view of the spherical unit permanent magnet 12a in FIG. 11 along a line 11-11 is shown in FIG. 12A, and a cross sectional view along a line 12-12 is shown in FIG. 12B. The structure may be made such that the spherical unit permanent magnets 12a, 12b, 12c . . . are magnetically attracted with each other on the peripheral surfaces (the side surfaces) R thereof so that the whole is formed in a ring shape.

An example shown in FIGS. 13 and 14 is structured such that the unit permanent magnets 13a, 13b, 13c . . . are formed in a flat shape (an oval shape), and are magnetically attracted with each other on the lateral side surfaces R in place of the vertical ends G as shown in FIG. 14, thereby forming the permanent magnet ring.

An example shown in FIGS. 15A and 15B is structured such that the unit permanent magnets 14a, 14b, 14c . . . are formed in a disc shape, and are magnetically attracted with each other by the side surfaces R in place of the disc-shaped end surface G as shown in FIG. 15B, thereby forming the permanent magnet ring.

An example shown in FIGS. 16A and 16B is structured such that the unit permanent magnets 15a, 15b, 15c . . . are formed in an approximately rectangular shape in a plan view, and are magnetically attracted with each other on the rounded side surfaces R, thereby forming the permanent magnet ring. The other shapes of the unit permanent magnet include a shape in which a cross section is an oval shape and an entire shape is an oval column shape, and a shape in which a cross section is a polygonal shape more than a pentagonal shape and an entire shape is a rectangular column shape.

The embodiment of the permanent magnet ring 1 in accordance with the present invention mentioned above may be structured as far as the permanent magnet ring is formed in a ring shape as the whole by magnetically attracting the unit permanent magnets 5a, 5b, 5c . . . or 6a, 6b, 6c . . . , 7a, 7b . . . , or 12a, 12b, 12c . . . , 13a, 13b, 13c . . . , 14a, 14b, 14c . . . , 15a, 15b, 15c . . . having the predetermined shape with each other on the respective side surfaces R, that is, the ring of the permanent magnet is formed, and is used for facilitating the flow of blood in the portion to be worn in the human body owing to the effect of the line of magnetic force. Further, various methods can be employed for manufacturing the unit permanent magnet, so that an isotropic magnet or an anisotropic magnet can be employed for the unit permanent magnet, however, it is desirable to employ the uniaxial anisotropic magnet. A description will be given below of a method of manufacturing the unit permanent magnet employing the uniaxial anisotropic magnet and the ring with reference to FIG. 17.

Figure 17:
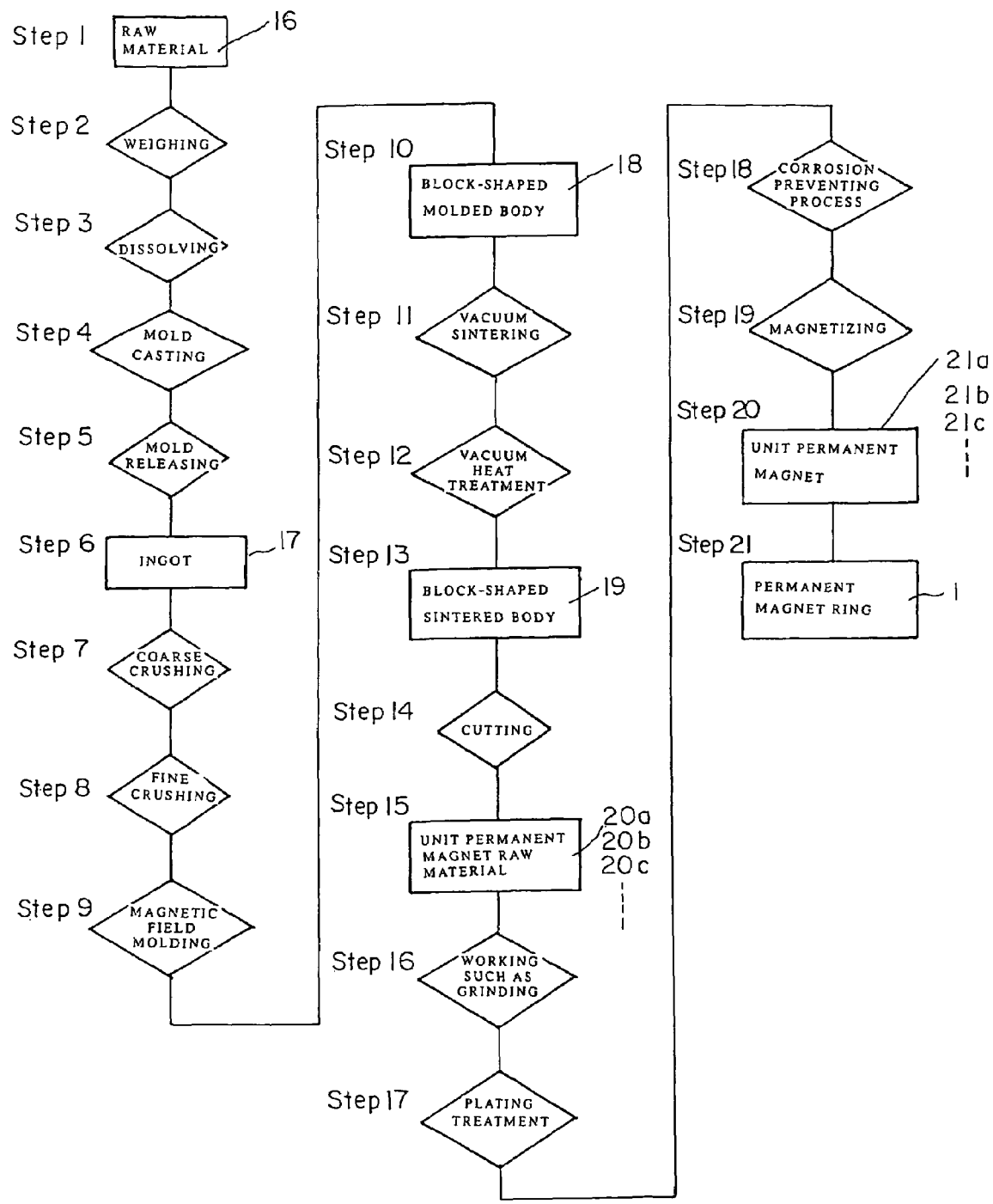
FIG. 17 is a view showing a manufacturing step of a uniaxial anisotropic unit permanent magnet and a permanent magnet ring.

FIG. 17 shows a manufacturing step view. First, a raw material 16 is prepared in step 1.

As the raw material, there is employed, for example, Nd—Fe—B (neodymium-iron-boron) based or Sm—Co (samarium-cobalt) based material. In the case of Nd—Fe—B based material mentioned above, in accordance with one example, there is employed a raw material having a compounding ratio by weight of Nd 26%, Fe 68%, B 2%, Dy (dysprosium) 3%, and Tb (terbium) 1%. In the case of Sm—Co, there can be listed up an example employing Sm and $Co_5$ and an example employing Sm and $Co_{17}$. In the case of $SmCO_5$ mentioned above, there is employed a raw material having a compounding ratio by weight of Sm 34 to 37% and $Co_5$ 66 to 63%. Further, in the case of $SmCo_{17}$ based material, there is employed a raw material having a compounding ratio by weight of Sm 20 to 28%, Fe 10 to 20%, Cu 3 to 15% and $Co_{17}$ 67 to 37%. In this case, the compounding ratio may be appropriately changed.

Next, after weighing in step 2, the raw material is dissolved at a temperature of about 1000° C. to 1500° C. in accordance with a high frequency dissolving method on the basis of an induction heating in step 3, is casted by mold as shown in step 4, and is released from the mold in step 5, and an ingot 17 is obtained in step 6. Thereafter, a coarse crushing and a fine crushing are executed in step 7 and step 8. For example, the material is crushed into grains of 50 # under by using a jaw crusher and is crushed into grains of 200 # under by using a hammer mill.

Thereafter, a magnetic field molding is executed in step 9.

Figure 18:
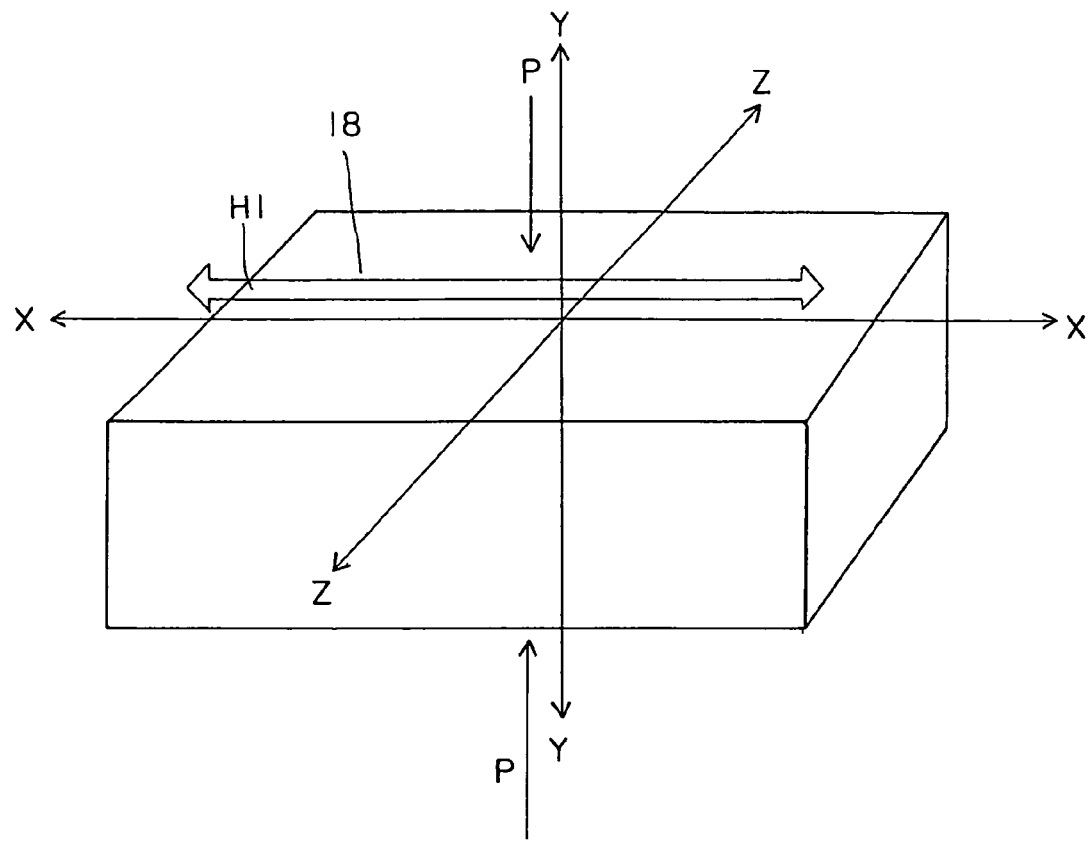
FIG. 18 is a view showing a magnetic field molding of step 9 in the manufacturing step in FIG. 17.
Figure 19:
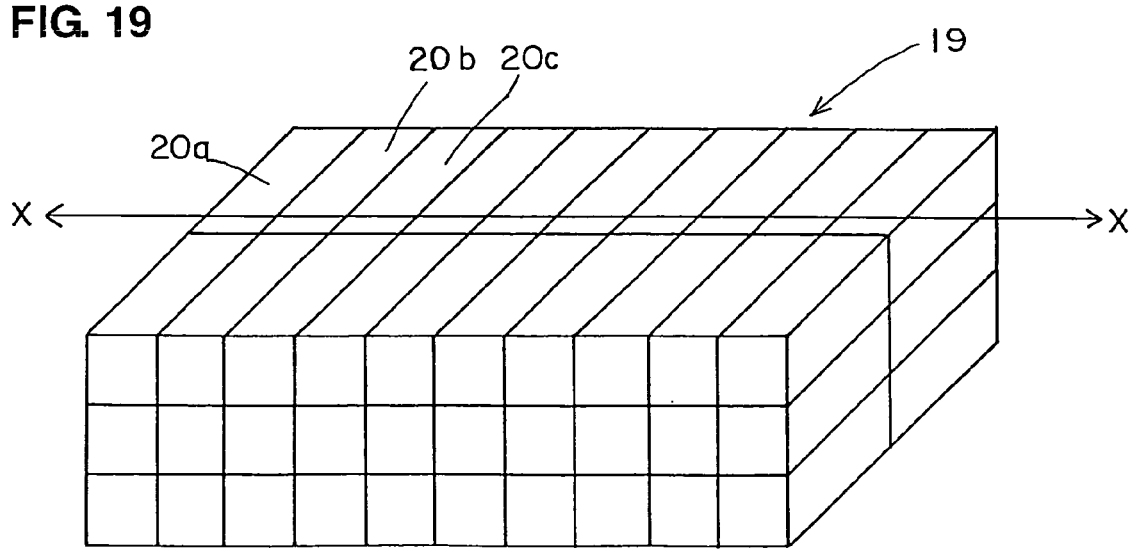
FIG. 19 is a view showing a block sintered body cutting of step 14 in the manufacturing step in FIG. 17.

A schematic view of the magnetic field molding is shown in FIG. 18. As shown in FIG. 18 of the schematic view, three dimensional directions of a molded body 18 are shown by X-X axis, Y-Y axis and Z-Z axis. While applying a press are P along any one axis of the three dimensions, for example, the Y-Y axis vertically, a magnetic field H1 is applied along another axis of the three dimensions, for example, the X-X axis, an easily magnetizing direction is formed in the direction along the X-X axis, and crystals are aligned in the easily magnetizing direction X-X.

Accordingly, the block-shaped molded body 18 is obtained as shown in step 10, and a vacuum sintering is applied under a condition of $10^{-5}$ to $10^{-6}$ Torr and 1150° to 1200° C. and a vacuum heat treatment is applied under a condition of 800 to 900° C. in accordance with a normal method in the order of steps 11 and 12.

A block-shaped sintered body 19 is thereby produced.

Figure 20:
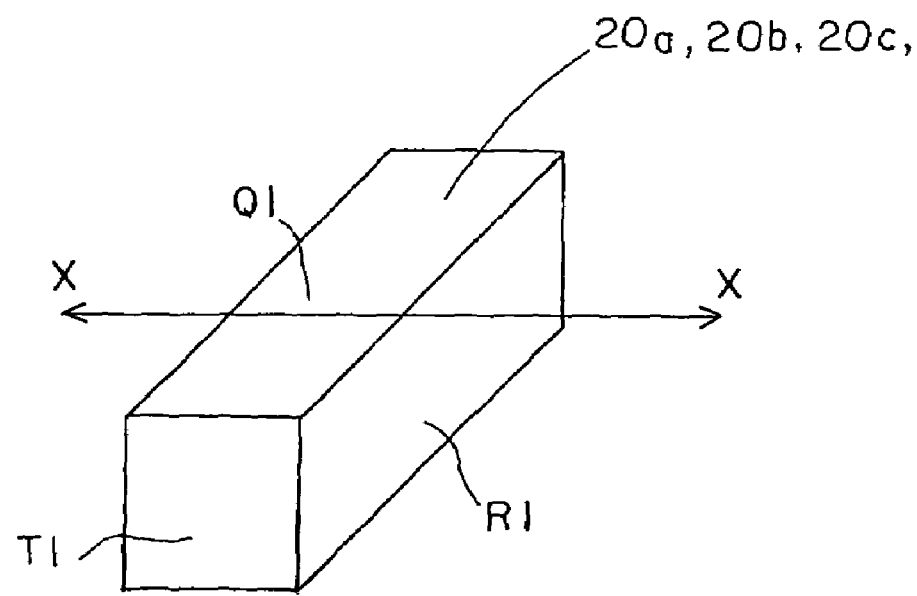
FIG. 20 is a view showing a unit permanent magnet raw material obtained by the cutting step in FIG. 19.

Thereafter, the block-shaped sintered body 19 is cut into pieces, and the unit permanent magnet raw materials 20a, 20b, 20c . . . are obtained as shown in step 15. In this cutting, the block-shaped sintered body 19 is cut such that a lateral side surface, a vertical surface and a longitudinal surface of each of the permanent magnet raw materials 20a, 20b, 20c . . . are aligned with the X-X axis, the Y-Y axis and the Z-Z axis. In other words, when giving symbols T1, R1 and Q1 to the longitudinal surface of one unit permanent magnet raw material 20a, 20b or 20c, the side surface thereof and the vertical surface thereof respectively as shown in FIG. 20, the vertical surface Q1 is in parallel to the X-X axis corresponding to the easily magnetizing direction, the longitudinal surface T1 is in parallel thereto, and the lateral side surface R1 is orthogonal thereto. In other words, in the unit permanent magnet raw materials 20a, 20b, 20c . . . , the easily magnetizing direction X-X is determined from one side surface toward another side surface.

Figure 21:
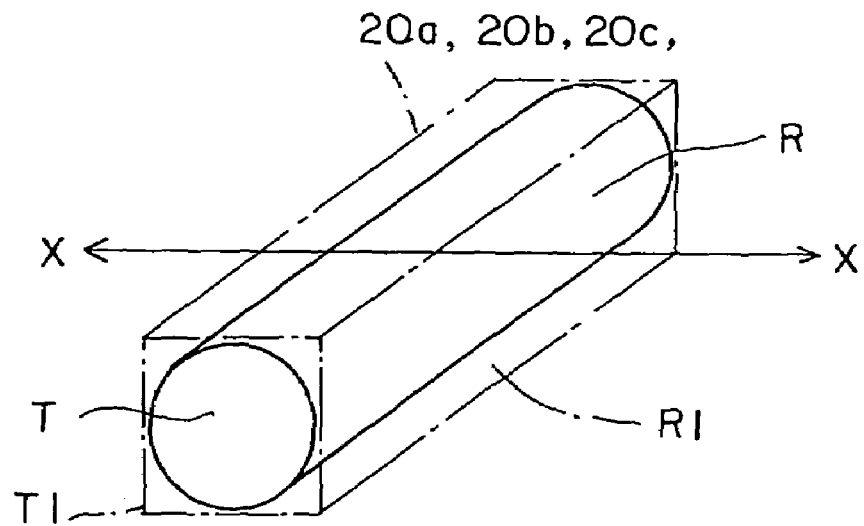
FIG. 21 is a view showing a grinding process of step 16 in the manufacturing step in FIG. 17.

Thereafter, as shown in step 16 and a schematic view in FIG. 21, a machine work is executed. In this embodiment, there is shown an example in which each of the aspects of the cylindrical unit permanent magnet shown in FIGS. 1 to 10 is worked. Since the unit permanent magnet raw materials 20a, 20b, 20c . . . cut into pieces are originally formed in the rectangular columnar shape, the lateral side surface R1 and the vertical surface Q1 are worked into a cylindrical shape in accordance with a grinding work or a polishing work as shown by a one-dot chain line in FIG. 21. Reference symbol R denotes a peripheral surface (a side surface) worked into the cylindrical shape. As is known from FIG. 21, a direction from the center of the cylindrical shape toward the peripheral surface R, that is, a radial direction coincides with the easily magnetizing direction X-X. Thereafter, a necessary chamfering work or the like is appropriately applied.

Next, a plating treatment is applied in step 17. In accordance with a normal way, an oxide, a fat and oil and the like are removed from the surface of the cylindrically worked unit permanent magnet raw material 20a, 20b, 20c . . . , and a base layer is first formed in accordance with an electrolytic plating method.

As one example, the base layer of Ni—Cu—Ni is formed at a thickness of 20 to 25 micron. Next, the gold or platinum rhodium plating layer 10 is formed at a thickness of 1 to 1.5 micron.

The surface ornament thereon such as the gold ornament, the platinum ornament and the like can be made in an appropriate way. In other words, the material and the coating layer forming means can be variously selected in correspondence to a chemical stability, a heat resistance, a workability and the like.

When wearing the permanent magnet ring 1 on the wrist, the portion around the neck and the like, it is necessary to prevent a corrosion due to sweating of the human body or natural deterioration and it is necessary to improve brilliance keeping. Therefore, a transparent coating layer 11 is formed by coating a siliceous coating material having a silica ($SiO_2$) as a main component, for example, at a thickness of 1 micron as shown in step 18 in accordance with a spraying method or a dipping method.

Accordingly, the ornament on the surface can be maintained for a long time.

Figure 22:
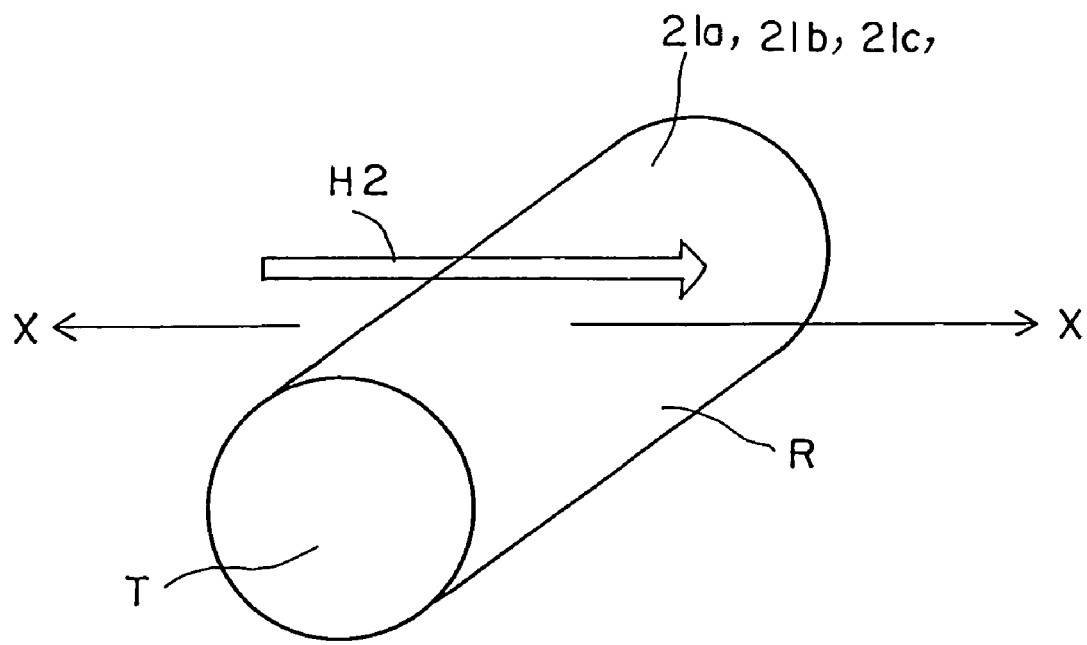
FIG. 22 is a view showing a cylindrical unit permanent magnet magnetizing step of step 19 in the manufacturing step in FIG. 17.

Subsequently, magnetizing is carried out so as to obtain the unit permanent magnet as shown in step 19 and FIG. 22. Magnetizing is carried out by applying a magnetic field H2 along the easily magnetizing direction X-X. While various magnetizing methods can be employed, one of the methods can be performed by using a pulse power source.

Accordingly, it is possible to manufacture the cylindrical unit permanent magnets 21a, 21b, 21c . . . .

In the cylindrical unit permanent magnets 21a, 21b, 21c . . . , since the easily magnetizing direction X-X is the diametrical direction orthogonal to the cylindrical axis, one part of the peripheral surface R is the N pole, and another part positioned in the opposite in the diametrical direction is the S pole.

Figure 23:
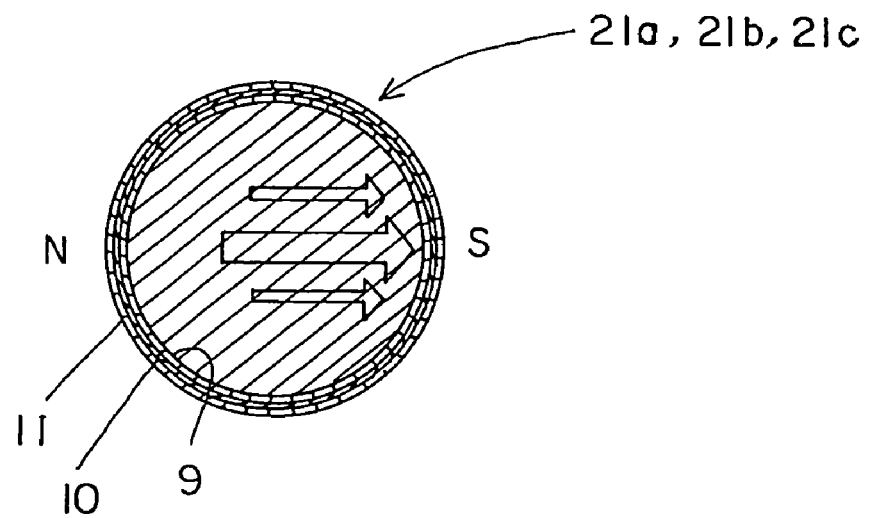
FIG. 23 is a cross sectional view of the cylindrical unit permanent magnet magnetized on the uniaxial anisotropic magnet in accordance with the magnetizing step in FIG. 22.

Since the magnet is formed as an anisotropic magnet magnetized along the easily magnetizing direction X-X, it is possible to obtain a strong magnet. Further, since the easily magnetizing direction X-X is along a radial direction of the unit permanent magnets 21a, 21b, 21c . . . , a strong magnetic force appears in a part of the peripheral surface along the easily magnetizing direction as shown in the schematic view in FIG. 23. Accordingly, the cylindrical unit permanent magnets 21a, 21b, 21c . . . are magnetically bonded to each other in a part of the peripheral surface R along the easily magnetizing direction without being bonded to each other on the end surface T. Accordingly, the cylindrical unit permanent magnets 21a, 21b, 21c . . . are magnetically bonded to each other in a part of the peripheral surface R along the easily magnetizing direction, are formed in a ring shape and form the permanent magnet ring 1 as shown in step 21.

Figure 24:
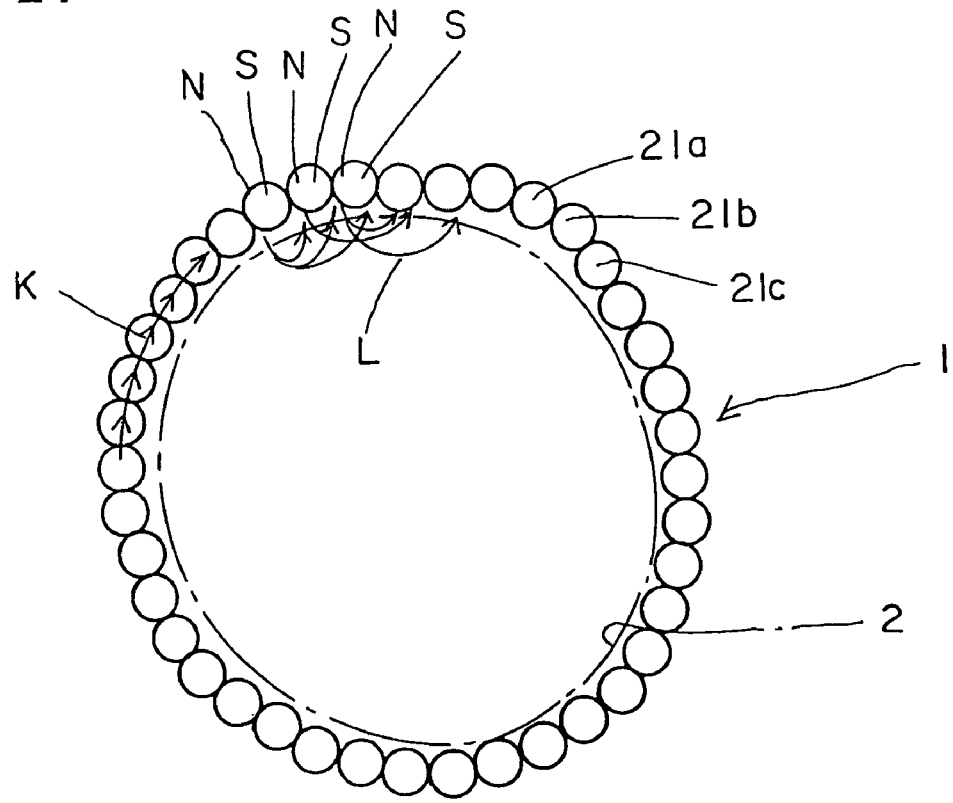
FIG. 24 is an explanatory view of a closed magnetic circuit and a leakage flux in the case of magnetically attracting a plurality of uniaxial anisotropic unit permanent magnets manufactured in accordance with the magnetizing step in FIG. 22 to each other so as to form a permanent magnet ring.

Since the unit permanent magnets 21a, 21b, 21c . . . are the anisotropic magnets, and the rare earth is employed as the raw material, the unit permanent magnets are formed to be strong uniaxial anisotropic magnets. Accordingly, in the case of the unit permanent magnets 21a, 21b, 21c . . . being magnetically attracted each other on the side surface (the cylindrical peripheral surface) along the cylindrical easily magnetizing direction so as to form the permanent magnet ring 1, the magnetic attracting force for keeping the ring shape is strong, so that in the case of wearing the permanent magnet ring 1 on the wrist or the like, there is no fear that the permanent magnet 1 falls away even by shaking the arm or the like. Here, in the case of wearing the permanent magnet ring 1 on the wrist 2 or the like as shown in FIG. 24, the unit permanent magnets 21a, 21b, 21c . . . mentioned above are magnetically attracted each other on the respective peripheral surfaces (the side surfaces) strongly as mentioned above, and, since the unit permanent magnets 21a, 21b, 21c . . . are attracted each other in the ring shape or the circle shape, the magnetic flux forms a closed magnetic path K. Accordingly, the magnetic force lines are not applied directly to the wrist 2 or the like.

The leakage flux L is applied to the wrist 2. Accordingly, the strong magnetic force effect is not applied to the human body and any unexpected side effect is not caused in the human body. It is possible to facilitate the flow of blood by the magnetic effect of the leakage flux without causing the side effect.

In this case, if the magnetic connection between the unit permanent magnets is strengthened for the purpose of preventing the shape of the permanent magnet ring from being lost and preventing the permanent magnet from falling away, the magnetic force effect being so rich in a magnetic flux density as to make the strong magnetic connection is generated, and there is a risk that an unexpected side effect is caused in the human body. On the contrary, if the magnetic strength of magnetizing is set to a level proper for the human body and applying just good magnetizing effect for facilitating the flow of blood, the magnetic connection between the unit permanent magnets is weak, so that there is a risk that the shape of the permanent magnet ring is lost and the unit permanent magnet falls away. As mentioned above, there is an irreconcilable point. However, since the present invention is structured such that the unit permanent magnets are constituted by the uniaxial anisotropic magnets and are formed in the ring shape, the unit permanent magnets are magnetically attracted each other strongly on the side surfaces, the effect of magnetic force lines caused by the strong magnetical attraction is not directly applied to the wrist or the like due to the closed magnetic path, but the leakage flux from the N pole toward the S pole between the unit permanent magnets 21a, 21b, 21c . . . is applied to the wrist or the like. Accordingly, a suitably restricted strength is applied. Even being restricted, since the magnetic force is set to be in the strength capable of magnetically connecting the unit permanent magnets strongly and the leakage flux results from such magnetic force, the leakage flux can sufficiently facilitate the flow of blood without causing the unexpected side effect.

Figure 25:
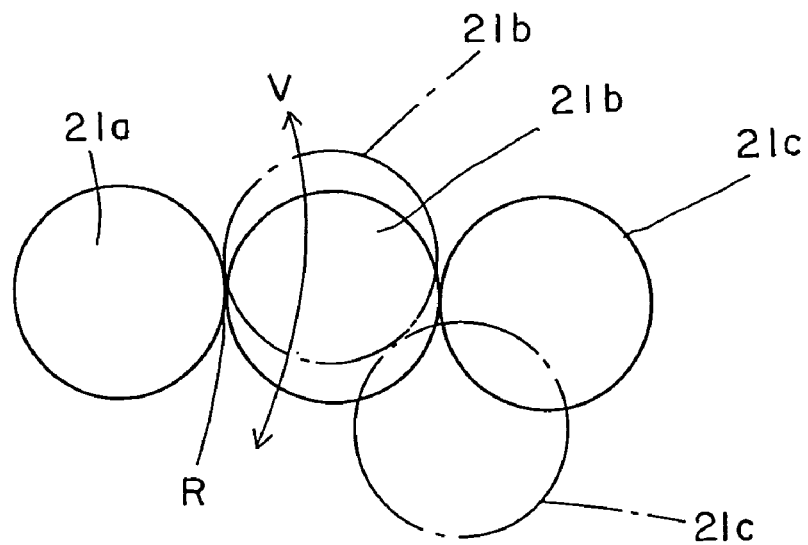
FIG. 25 is an explanatory view of a magnetic attarcting relation between the uniaxial anisotropic cylindrical unit permanent magnets.

Further, since the unit permanent magnets 21a, 21b, 21c . . . are constituted by the uniaxial anisotropic magnets as mentioned above, the unit permanent magnets 21a, 21b, 21c . . . are magnetically connected to each other strongly on the side surfaces along the easily magnetizing direction of the cylindrical side surface. In view of the aspect thereof, the unit permanent magnets 21a, 21b, 21c . . . are connected to each other in accordance with a line contact along the cylindrical axial direction on the peripheral surface (the side surface) R as shown in FIG. 25. Accordingly, although a great force is required for falling away against the direction of the magnetic connection, the unit permanent magnet can move in a direction not corresponding to the falling away direction (a non-falling away direction) as shown by an arrow V such as from a state illustrated by a solid line to a state illustrated by a one-dot chain line on the basis of an extremely weak force. Therefore, as well as it is easy to form in the ring shape, it is easy to change the number of the unit permanent magnets so as to change the size of the ring.

A residual flux density (Br) on the side surfaces attracted each other in the particular example of the cylindrical permanent magnets 21a, 21b, 21c . . . mentioned above is set preferably to 6 KG to 15 KG in CGS System of units (0.6 T to 1.5 T in International System of units). In the case of the permanent magnets being worn on the human body, a surface flux density in the portion contacted with the skin of the human body, that is, the leakage flux density (Br) is preferably set to 35 mT to 200 mT in International System of units, a coercive force ($H_{CB}$) is preferably set to 10 KOe to 40 Koe in CGS System of units, and a maximum energy product (BH)max is preferably set to a range between 12 to 50 MGOe in CGS System of units.

Figure 26:
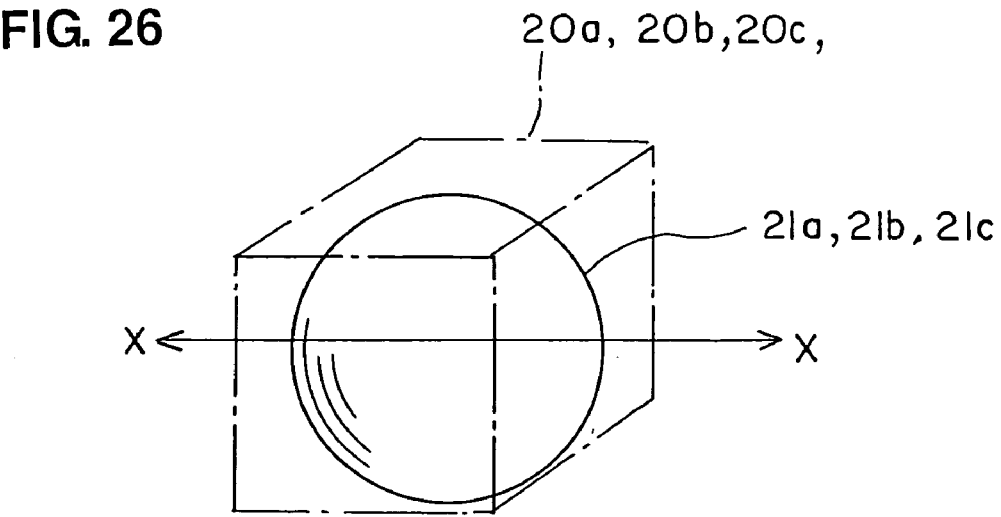
FIG. 26 is a view for explaining a process of a uniaxial anisotropic spherical unit permanent magnet.
Figure 27:
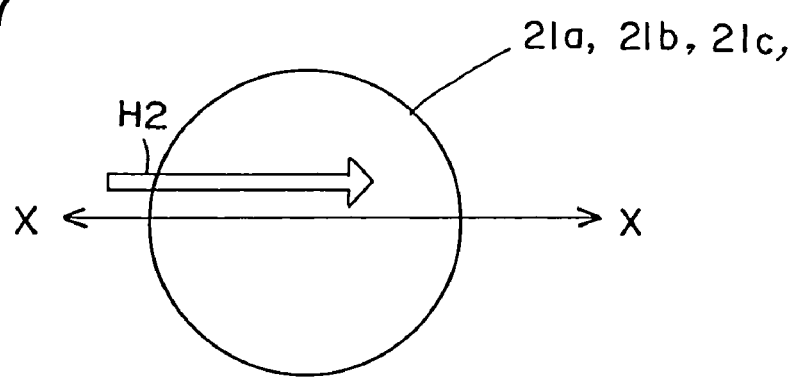
FIG. 27 is a view of the uniaxial anisotropic spherical unit permanent magnet.
Figure 28:
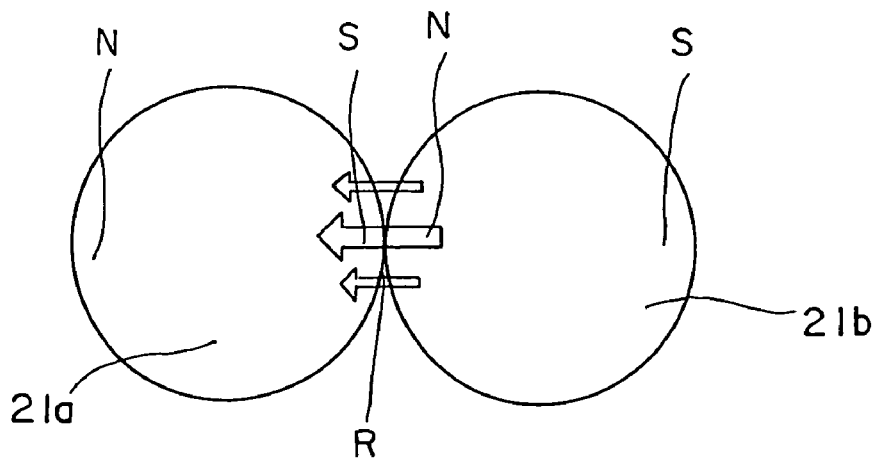
FIG. 28 is a view explaining the magnetic attraction between the uniaxial anisotropic spherical unit permanent magnets.

The embodiment mentioned above is the example of the cylindrical unit permanent magnet, however, even in the case of the spherical shape shown in FIGS. 26 to 28, the uniaxial anisotropic permanent magnet can be employed.

In this case, the easily magnetizing direction of the sintered unit permanent raw materials 20a, 20b, 20c . . . is set to X-X, the raw material defined in the manner mentioned above is ground into the spherical shape, the plating process and the siliceous transparent coating layer forming are thereafter applied, and the magnetizing is then performed by applying the magnetic field H2 along the easily magnetizing direction X-X.

Accordingly, one portion of the peripheral surface (the side surface) R of the spherical unit permanent magnets 21a, 21b, 21c . . . forms the N pole, and another portion positioned at the opposite side in the diametrical direction forms the S pole, so that it is possible to work the strong uniaxial anisotropic spherical permanent magnet.

In the case of the embodiment, the spherical unit permanent magnets 21a, 21b, 21c . . . are magnetically attracted each other strongly in the same manner as that of the cylindrical permanent magnet. In the case that a lot of the unit permanent magnets are connected in a circle shape so as to form the permanent magnet ring, the closed magnetic circuit is formed and no unexpected effect is applied to the human body even when the strongly attracting magnetic force is generated. In other words, magnetic force lines applied to the arm of the human body is in the aspect of the leakage flux, and a suitable effect is achieved.

In addition, since the unit permanent magnets are magnetically attracted each other between parts of the spherical peripheral surfaces in accordance with a point contact aspect, it is possible to freely and easily change the magnetic attracting positions between the spherical unit permanent magnets 21a, 21b, 21c . . . .

Figure 29:
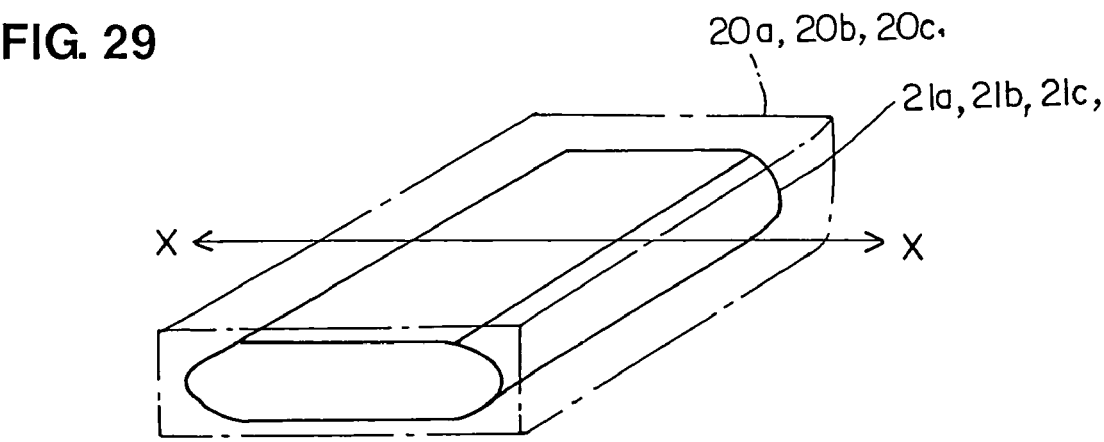
FIG. 29 is a view explaining a processing of the uniaxial anisotropic flat unit permanent magnet.
Figure 30:
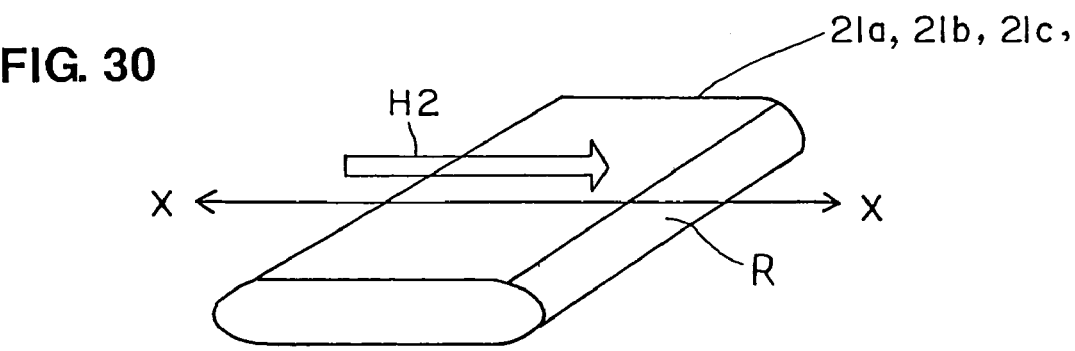
FIG. 30 is a view of the uniaxial anisotropic flat unit permanent magnet.
Figure 31:
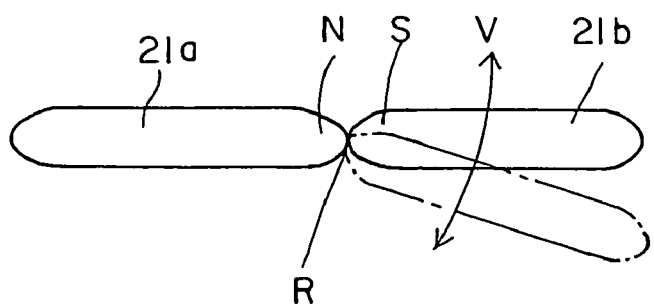
FIG. 31 is an explanatory view of the magnetic attraction between the uniaxial anisotropic flat unit permanent magnets.

Next, in the case of a flat shape shown in FIGS. 29 to 31, it is also possible to obtain a uniaxial anisotropic permanent magnet.

The easily magnetizing direction of the sintered unit permanent raw materials 20a, 20b, 20c . . . is set to X-X, the raw material defined in the manner mentioned above is ground into the flat shape, the plating process and the siliceous transparent coating layer forming are thereafter applied, and the magnetizing is then performed by applying the magnetic field H2 along the easily magnetizing direction X-X.

Accordingly, one portion of the side surfaces R of the flat unit permanent magnets 21a, 21b, 21c . . . forms the N pole, and another side surface R positioned at the opposite side forms the S pole, so that it is possible to work the strong uniaxial anisotropic flat permanent magnet.

In the case of the embodiment, the flat unit permanent magnets 21a, 21b, 21c . . . are magnetically attracted each other strongly in the same manner as that of the previous examples. In the case that a lot of the unit permanent magnets are connected in a circle shape so as to form the permanent magnet ring, the closed magnetic circuit is formed and no unexpected effect is applied to the human body even when the strongly attracting magnetic force is generated. In other words, the magnetic force lines applied to the arm of the human body is in the aspect of the leakage flux, and a suitable effect is achieved.

In addition, since the unit permanent magnets are magnetically attracted each other between parts of the flat side surfaces in accordance with a line contact aspect, it is possible to freely and easily change the magnetic attracting positions between the flat unit permanent magnets 21a, 21b, 21c . . . . Since the side surface R is formed in a curved surface (a rounded surface), the flat unit permanent magnets 21a, 21b, 21c . . . are magnetically attracted each other in accordance with the line contact aspect as mentioned above.

What is claimed is:

1. A permanent magnet ring comprising a plurality of unit permanent magnets, each having a cylindrical shape, a flat shape, or a disc shape, a predetermined number of said unit permanent magnets being magnetically attracted to each other so as to be formed into a ring shape;

wherein each of said unit permanent magnets comprises a neodymium iron boron magnet core and a plated layer formed on the surface thereof;

wherein said each unit permanent magnet is a uniaxial anisotropic magnet in which an N pole or an S pole is formed on a first side surface of said uniaxial anisotropic magnet orthogonal to an easily magnetizing direction, while an S pole or an N pole is formed on a second side surface of said uniaxial anisotropic magnet opposite to said first side surface, said easily magnetizing direction is formed at a time of sintering a raw material of the neodymium iron boron magnet in a magnetic field, said N and S poles are magnetized along said easily magnetizing direction after sintering, and said first and second side surfaces are formed into curved surfaces;

wherein a predetermined number of said unit permanent magnets are magnetically attracted to each other in a line contact manner on the curved first and second side surfaces on which said N and S poles are formed by magnetizing along said easily magnetizing direction after sintering, and the S pole or the N pole is formed, thereby forming a ring shape having a predetermined size;

wherein a magnetically attracting force on said N and S poles is strong and said unit permanent magnets are strongly connected with each other in a line contact manner such that the ring shape can be kept as a whole because said unit permanent magnets are uniaxial anisotropic magnets; and wherein a magnetic flux from the magnetic poles of each of said unit permanent uniaxial anisotropic magnets forms a closed magnetic path along the circumference of the permanent magnet ring so that the magnetic flux does not act directly on the area inside of the permanent magnet ring despite the strong magnetically attracting force, a leakage magnetic flux acts on the area inside of the permanent magnet ring and magnetic action caused by the leakage magnetic flux density is restrained to be weak as compared to the magnetic action caused by the magnetic flux from the magnetic poles forming the closed magnetic path and which are due to the uniaxial anisotropic nature of said unit permanent magnets; and wherein said leakage magnetic flux density is 35 mT to 200 mT.

2. A permanent magnet ring comprising a plurality of unit permanent magnets, each having a spherical shape, a predetermined number of said unit permanent magnets being magnetically attracted to each other so as to be formed into a ring shape;

wherein each of said unit permanent magnets comprises a neodymium iron boron magnet core and a plated layer formed on the surface thereof;

wherein said each unit permanent magnet is a uniaxial anisotropic magnet in which an N pole or an S pole is formed on a side surface of said uniaxial anisotropic magnet orthogonal to an easily magnetizing direction, while an S pole or an N pole is formed on another side surface of said uniaxial anisotropic magnet opposite to said first side surface, said easily magnetizing direction is formed at a time of sintering a raw material of the neodymium iron boron magnet in a magnetic field, said N and S poles are magnetized along said easily magnetizing direction after sintering, and said first and second side surfaces are formed into curved surfaces;

wherein a predetermined number of said unit permanent magnets are magnetically attracted to each other in a point contact manner on the curved first and second side surfaces on which said N and S poles are formed by magnetizing along said easily magnetizing direction after sintering, and the S pole or the N pole is formed, thereby forming a ring shape having a predetermined size;

wherein a magnetically attracting force on said N and S poles is strong and said unit permanent magnets are strongly connected with each other in a point contact manner such that the ring shape can be kept as a whole because said unit permanent magnets are uniaxial anisotropic magnets; and wherein a magnetic flux from the magnetic poles of each of said unit permanent uniaxial anisotropic magnets forms a closed magnetic path along the circumference of the permanent magnet ring so that the magnetic flux does not act directly on the area inside of the permanent magnet ring despite the strong magnetically attracting force, a leakage magnetic flux acts on the area inside of the permanent magnet ring and magnetic action caused by the leakage magnetic flux density is restrained to be weak as compared to the magnetic action caused by the magnetic flux from the magnetic poles forming the closed magnetic path and which are due to the uniaxial anisotropic nature of said unit permanent magnets; and wherein said leakage magnetic flux density is 35 mT to 200 mT.

3. A permanent magnet ring as claimed in any one of claims 1 or 2, wherein each of said unit permanent magnets further comprises a transparent siliceous coating layer formed over said plated layer formed on said neodymium iron boron magnet core.

* * * * *